US012778849B2

(12) United States Patent
Sicard et al.

(10) Patent No.: US 12,778,849 B2
(45) Date of Patent: Nov. 3, 2026

(54) DRUG DISPENSING DEVICE, SYSTEM AND METHOD

(71) Applicant: THESS CORPORATE, Montpellier (FR)

(72) Inventors: Roland Sicard, Juvignac (FR); Yves Boge, Sussargues (FR)

(73) Assignee: THESS CORPORATE, Montpellier (FR)

( * ) Notice: Subject to any disclaimer, the term of this patent is extended or adjusted under 35 U.S.C. 154(b) by 333 days.

(21) Appl. No.: 18/294,315

(22) PCT Filed: Aug. 4, 2022

(86) PCT No.: PCT/EP2022/072010
§ 371 (c)(1),
(2) Date: Feb. 1, 2024

(87) PCT Pub. No.: WO2023/012306
PCT Pub. Date: Feb. 9, 2023

(65) Prior Publication Data

US 2024/0335356 A1 Oct. 10, 2024

(30) Foreign Application Priority Data

Aug. 5, 2021 (FR) ...................................... 2108527

(51) Int. Cl.
*A61J 7/00* (2006.01)
*G16H 20/13* (2018.01)

(52) U.S. Cl.
CPC ............ *A61J 7/0076* (2013.01); *G16H 20/13* (2018.01); *A61J 2205/60* (2013.01)

(58) Field of Classification Search
CPC .... A61J 7/0076; A61J 2205/60; A61J 1/1437; A61J 1/03; A61J 1/05; A61J 2200/30; A61J 2200/72; A61J 2200/70; A61J 1/18; G16H 20/13; G06Q 20/4015; G07F 9/001; G07F 11/005; G07F 11/44; G07F 17/0092
See application file for complete search history.

(56) References Cited

U.S. PATENT DOCUMENTS 10,722,431 B2 * 7/2020 Chen ..................... A61J 7/0418
2018/0271752 A1 9/2018 Iordanov et al.
(Continued)

FOREIGN PATENT DOCUMENTS

CN 206384803 U * 8/2017

OTHER PUBLICATIONS

International Search Report and Written Opinoin received for PCT/EP2022/072010, mailed Nov. 11, 2022.
(Continued)

*Primary Examiner* — Jacob S. Scott
*Assistant Examiner* — Miraj T. Patel
(74) *Attorney, Agent, or Firm* — Greer, Burns & Crain, Ltd

(57) ABSTRACT

A device for packaging, conveying and/or dispensing drugs for a user, including a closed drug container intended to receive at least one drug to be dispensed and including a drug-dispensing opening which is intended to be opened when dispensing a drug, and at least one sensor that is sensitive to at least one physical quantity within the container that may affect the integrity of the at least one drug located in the container is disclosed. A drug-dispensing system using such a device is also disclosed.

20 Claims, 6 Drawing Sheets

(56) References Cited

U.S. PATENT DOCUMENTS

| | | | | |
|---|---|---|---|---|
| 2018/0280553 | A1 | 10/2018 | Leupold et al. | |
| 2020/0060931 | A1 | 2/2020 | Carrico | |
| 2021/0205180 | A1 | 7/2021 | Pugsley | |
| 2021/0319872 | A1 * | 10/2021 | Valentine ............... | G16H 40/67 |

OTHER PUBLICATIONS

French Search Report received for Application No. 2108527, dated Mar. 29, 2022.

* cited by examiner

DRUG DISPENSING DEVICE, SYSTEM AND METHOD

BACKGROUND

The present invention relates to a device for dispensing a drug to a user. It also relates to a system for dispensing a drug implementing such a device.

The field of the invention is the field of the devices for packaging, transporting and dispensing drugs.

There are currently several devices for dispensing drugs. Most frequently, these devices are presented in the form of an appliance that delivers a dose of a drug to a user, or a box comprising drugs in sachets or blisters. Some of these devices are presented in the form of a case containing several compartments each comprising a certain quantity of drugs. Other dispensing devices incorporate a mechanism delivering a certain quantity of a drug from a container for a drug, possibly with a mechanical control of the quantity of the drug delivered at each use of said device.

In any event, the user is generally alone at the time the drug is taken. There is no means of verifying and ensuring the integrity of the drug present in the dispensing device. This gives rise to potential risks of a drug being taken, the integrity of which has been compromised for various reasons, the consequences of which can be serious and detrimental to the health of the user, sometimes irreversibly.

An aim of the present invention is to overcome this drawback.

Another aim of the invention is to propose a device for dispensing drugs that is more secure and presents a lower risk to the user in comparison with the current devices.

SUMMARY

The invention proposes to achieve at least one of the aforementioned aims by means of a device for packaging, transporting and/or dispensing a drug comprising:

- a closed container for a drug, provided to receive at least one drug to be dispensed and comprising an opening for dispensing a drug, intended to be released when a drug is dispensed; and
- at least one sensor sensitive to at least one physical quantity within said container capable of affecting the integrity of said at least one drug present in said container.

The invention thus proposes a device comprising a container in which is placed at least one drug that is then delivered to a user. According to the invention, the device comprises one or more sensors, each sensitive to one or more physical quantities inside the container and capable of affecting the integrity of the drug that is present in the container. Thus, at any time and in particular at the time of dispensing the drug contained in the container, it is possible to determine if said at least one drug has been subjected to physical conditions that may at least potentially have degraded the integrity of the drug or drugs. As a result, the device according to the invention makes it possible to dispense drugs more securely and with a lower risk to the user in comparison with the current devices.

The dispensing opening can be closed by any suitable means, such as for example a cap, a membrane, a lid, etc., sealing or not.

The dispensing opening can be released at the time of first use of the device according to the invention.

Release of the dispensing opening can be carried out by tearing the membrane, or by removing the cap, which closes it, etc.

The drug to be dispensed can be in liquid form. In this case, the container is closed in a liquid-tight manner, and in particular watertight, for example by a cap, a membrane or a lid that is liquid-tight, in particular watertight.

The drug to be dispensed can be in gaseous form. In this case, the container is closed in an airtight manner, for example by an airtight cap, membrane or lid.

Alternatively, the drug to be dispensed can be in solid form. In particular, the drug can be presented in powder form, in capsule or tablet form, etc. In this case, the container can be closed for example by a cap, a membrane or a lid, sealing or not.

According to embodiments, at least one sensor can be arranged in the container.

According to embodiments, at least one sensor can be arranged in or on a wall of the container.

For example, it is possible for at least one sensor not to open into the container. Thus, it is not affected by the drug present in the container, nor will it impair the drug present in the container.

Alternatively, or in addition, at least one sensor can open into the container, for example so as to allow a measurement associated with the state of the drug itself.

Alternatively, or in addition, at least one sensor can be arranged on an inner face of the wall and be partially or wholly located in the container. Such a positioning allows a greater sensitivity of the sensor to at least one physical quantity in the container.

At least one sensor can be arranged in a housing provided in said container.

Such a housing can be provided at any site in the container, can be non-sealing, or can be for example liquid-tight or airtight.

Advantageously, at least one sensor can be arranged in, or at the level of, an upper part of the container, in a configuration of use of said device during dispensing of the drug.

Such a positioning makes it possible to minimize the contact between the sensor and the drug present in the container. In addition, such a positioning makes it possible to facilitate exchanging data with the sensor, when the latter is a communicating sensor.

Advantageously, at least one sensor can be a sensor that degrades when the value of at least one physical quantity exceeds a threshold value.

In this case, the sensor no longer functions when the value of the physical quantity exceeds the threshold value, or communicates with a measurable variation in its response. For example, the sensor can no longer be read, or does not communicate any data item, or also does not measure any data item. This means that at least one of the physical quantities to which said sensor is sensitive has exceeded the threshold value defined for said quantity.

The threshold value can correspond to a limit beyond which the integrity or the quality of the drug present in the container is degraded. For example, the sensor can be sensitive to humidity. In this case, the sensor can be designed to degrade when the humidity ratio within the container reaches a threshold value. This threshold value can correspond to the maximum humidity value that the drug can withstand and beyond which the drug also degrades. The same reasoning applies for temperature, pressure, shocks, etc.

For at least one physical quantity, a maximum threshold value and/or a minimum threshold value can be defined.

According to embodiments, at least one sensor can comprise an RFID tag, comprising an electronic chip and an antenna, which can no longer be read, or the reading of which is affected, when the value of at least one physical quantity exceeds a threshold value.

Such a sensor comprises a component that degrades and that prevents the RFID tag being read by an external reader. This component can be the support materials of the antenna so as to affect the communication properties, such as for example a paper or a resin that is affected by humidity or temperature. Alternatively or in addition, the antenna can also be printed with an ink that is capable of fading under the effect of such and such a quantity, for example temperature.

Thus, provided that the value of the at least one physical quantity does not exceed at least one threshold value that is associated therewith, the RFID tag can be read. Otherwise, the RFID tag cannot be read.

The electronic chip can store any type of data items, in particular an identification data item of the device. Thus, provided that the identification data item of the device can be read, this means that the drug present in the container is not degraded. Otherwise, the drug present in the container has been degraded.

Advantageously, at least one sensor can be a sensor for measuring a value of at least one physical quantity.

In this case, unlike a degradable sensor, the measurement sensor continues to operate even when the value of the physical quantity reaches or exceeds a threshold value.

Such a sensor can be arranged to communicate the measured value to an appliance external to the device.

Alternatively or in addition, such a sensor can be arranged to communicate the measured value to a chip, or a memory, of the device according to the invention for storage thereof.

Non-limitatively, at least one sensor can be sensitive to at least one of the following quantities:

- temperature,
- pressure,
- hygrometry,
- movement, acceleration or shock,
- electrical, magnetic or electromagnetic radiation,
- pollution,
- time (elapsed time, wear, oxidation, etc.)
- luminosity.

At least one sensor can be sensitive to a single physical quantity.

At least one sensor can be sensitive to several physical quantities.

According to embodiments, the device according to the invention can comprise at least one sensor of a state of release or not of the dispensing opening.

Such a sensor can be any type of sensor, such as for example an optical sensor monitoring the state of the dispensing opening, a resistive sensor arranged at the dispensing opening and which is degraded when said opening is open, etc.

The device according to the invention can moreover comprise an electronic chip for storing at least one data item relating to the drug present in said container.

Such a chip can be coupled to, or be independent of, at least one sensor.

The electronic chip can be arranged in the container, in particular on a wall of the container, or also in a housing provided in said container.

The electronic chip can be arranged in the wall in a sealed manner, in particular liquid-tight, so that it is not impacted by the contents of the container, in particular when the drug is liquid.

In other versions, the electronic chip can be arranged in, or on, a part other than the container, when the device according to the invention comprises at least one part other than the container. For example, the electronic chip can be arranged on an electronic circuit board equipping the device according to the invention, a stand of the device according to the invention, a mechanical dispensing unit, etc. if applicable.

According to a preferred version, the electronic chip can be a chip:

- readable by a reader, or a reading unit, wired or wirelessly, and in particular at any time, and/or
- writable by an appliance, or a write unit, or also by a sensor equipping said device.

In particular, the electronic chip can be read and/or written to at any time during the life of the device according to the invention. Thus, at each time and at each of the steps of its manufacture, filling, transport and use, it is possible to write data items to the electronic chip.

At least one of the data items present in the chip can be tested, locally or remotely, to decide to dispense the drug or not, at a subsequent moment.

The electronic chip can be any type of chip comprising a memory space for storing the data items therein.

The electronic chip can be a read-only memory, a flash memory, a bulk store, an SSD, or any other type of memory (RAM, holographic memory, 3D X-Point, etc.).

The electronic chip can comprise or be coupled to a wired communication interface, such as a serial or parallel communication port, and/or a wireless communication interface such as an antenna.

According to a non-limitative embodiment example, the electronic chip can be an RFID chip, or a radio tag, comprising an electronic chip coupled to an antenna.

The at least one data item written to the electronic chip can be of any type.

At least one data item written to the electronic chip can relate to the drug present in the container, in particular at least one data item relating to the nature and composition of the drug.

Alternatively, or in addition, at least one data item written to the electronic chip can relate to the device according to the invention, and in particular to the manufacture and/or transport and/or identification thereof.

Alternatively, or in addition, the at least one data item written to the electronic chip can relate to the user, and in particular to their identification.

Alternatively, or in addition, at least one data item written to the electronic chip can relate to a dosage.

Alternatively, or in addition, at least one data item written to the electronic chip can relate to an identity of an actor, or an authentication, of at least one actor involved in the chain of preparation and/or delivery of said drug or of said device.

Alternatively, or in addition, the at least one data item written to the chip can comprise any combination of at least one of the following data items:

- at least one geolocation data item relating to the place of manufacture of the drug,
- at least one geolocation data item relating to the place of filling the container with the drug,
- at least one geolocation data item relating to the route travelled by the device according to the invention between its place of filling and its place of use by the user, etc.

Alternatively, or in addition, at least one data item written to the chip can comprise any combination of at least one of the following data items:

- at least one time stamp data item relating to the time of manufacture of the drug,
- at least one time stamp data item relating to the time of filling the container with the drug,
- at least one data item relating to the duration of the route travelled by the device according to the invention between its place of filling and its place of use by the user, etc.
- at least one data item relating to a validity period, or date, for consumption of said drug, etc.

Alternatively, or in addition, at least one data item written to the chip can comprise any combination of at least one of the following data items relating to the use of said drug:

- at least one data item relating to the dosage,
- at least one data item relating to the identity of the user to whom the drug must be delivered,
- etc.

At least one of the data items described above as being stored in the chip can alternatively be stored in a remote server, in particular in association with an identifier of the device.

Regardless of the storage site, at least one of these data items can be tested, locally or remotely, before the drug is dispensed, in order to allow said dispensing or not.

At least one data item can be written, to the chip or to the server, at any time.

For example, at least one data item can be written to the chip at the time of filling the container. This at least one data item can relate to the nature of the drug, the quantity of the drug, the manufacturer of the drug, the actor filling the drug, the time of filling the drug, a validity end date or period of the drug, an authentication number or digital certificate, etc.

Alternatively, or in addition, at least one data item can be written to the chip during conveyance of the device between its place of filling and its place of use. This at least one data item can relate to at least one route (place and/or date) travelled by the device according to the invention, a carrier of said device, a distributor of said device, etc.

Alternatively, or in addition, at least one data item can be written to the chip during the use of the drug, such as for example a quantity of the drug delivered during a step of dispensing a drug, an item of timestamp data of a dispensing step, an identifier of the user to whom the drug was dispensed during a dispensing step, etc.

The device according to the invention can moreover comprise at least one biometric reader for reading at least one biometric data item of a user, such as for example a digital fingerprint reader, at least one retinal scan, etc.

Such a biometric data item can be used to verify the identity of the user before dispensing the drug.

The at least one biometric reader can be arranged on the container.

Alternatively, the at least one biometric reader can be arranged in, or on, a part of said device other than the container, when the device comprises parts other than the container. For example, the at least one biometric reader can be arranged in, or on, an electronic circuit board of said device, when the device is equipped with such an electronic circuit board. According to another example, the at least one biometric reader can be arranged in, or on, a base of said dispensing appliance, when said appliance comprises such a base.

The device according to the invention can comprise at least one module for communication with a remote site, via a connection, wired or not, for sending and/or receiving data items.

Such a communication module can for example transmit data items relating to the identity of the device according to the invention to the remote site in order to obtain data items relating to the dispensing of the drug present in the container. These data items can comprise one or more conditions to be verified in order to dispense the drug, as well as the dosage of the drug.

The at least one communication module can be arranged on, or in, the container.

Alternatively, the at least one communication module can be arranged in, or on, a part of the device other than the container, when the device comprises parts other than the container. For example, the at least one communication module can be arranged in, or on, an electronic circuit board of said device, when the device is equipped with such an electronic circuit board. According to another example, the at least one communication module can be arranged in, or on, a base of said dispensing appliance, when the device is equipped with such a base.

Such a communication module can be a wireless communication module of the NFC, Wi-Fi, Bluetooth®, 3G, 4G, 5G type, or a wired communication module, for example of the Ethernet type.

According to a non-limitative embodiment example, the communication module can contain a module for communication over a phone network, such as for example a physical SIM card or SIM emulator.

The device according to the invention can moreover comprise a module for measuring a quantity of a drug exiting the container via the dispensing opening.

Such a module makes it possible to ensure that the quantity of the drug dispensed is in accordance with a predetermined dosage.

Such a module can comprise any type of sensor for measuring the quantity of the drug such as a weighing means, a means for counting a capsule or tablet, a means for measuring the volume of a drug, etc.

The device according to the invention can moreover comprise a closure means, in particular arranged downstream of the dispensing opening, which can be displaced between a first position allowing the passage of a drug through the dispensing opening and a second position preventing the passage of a drug through the dispensing opening.

Such a closure means can be controllable, for example by a control unit of said device, such that, when an abnormality is detected said closure means is positioned in its second position.

An abnormality can be associated with, or be deduced from, any one of the data items or parameters described above.

Such a closure means can comprise a controllable actuator provided to displace a member forming a physical obstacle to the passage of the drug, in the second position. The member forming a physical obstacle can be a tab, a mask, a cover, or any other object opposing the passage of the drug. The actuator can be a motor, or a cylinder, or also a magnetic actuator, or any other actuator capable of being controlled by an electrical signal, or a wave.

According to embodiments, the closure means can comprise a first mechanism, which can be displaced between an open position allowing the passage of a drug through the dispensing opening and a closed position preventing the passage of a drug through the dispensing opening, and provided to be actuated by the user.

Such a closure means can be actuated manually by the user, for example by a press on the device.

Non-limitatively, the first closure mechanism can be in closed position when it is idle, i.e. when no force is applied thereto. Thus, when idle no drug can be delivered. When the user actuates the first mechanism, for example by a press on the device, the first mechanism can pass into the open position, thus allowing the passage of a drug.

When the device according to the invention is presented in the form of a cartridge to be used with an appliance being presented in the form of a base, the first mechanism can preferably form part of said cartridge. Alternatively, the first mechanism can form part of said base.

According to an embodiment example that is in no way limitative, the first mechanism can comprise at least one shutter, in particular a double shutter forming a jaw. In the idle state, said shutter (or said jaw) is closed and opposes the passage of the drug. When the user actuates the first mechanism, for example by a press on the device, the shutter (or the jaw) moves away and allows the passage of (a) drug(s).

According to embodiments, the first mechanism can open and close in a plane parallel to the direction of passage of the drug.

Alternatively, or in addition to the first mechanism, the closure means can comprise a second mechanism, which can be displaced between an open position allowing the passage of a drug and a closed position preventing the passage of a drug, and provided to be actuated automatically.

The second mechanism can be controlled by a management unit of said device, for example according to at least one tested data item/condition, such as one of, or any combination of at least two of, the data items/conditions listed above.

The management unit can control the second mechanism by virtue of an actuator, such as a motor or a cylinder, and optionally via a movement transmission element, such as a drive shaft, a cam, a belt, etc.

When the device according to the invention is presented in the form of a cartridge to be used with an appliance presented in the form of a base, the second mechanism can preferably form part of said cartridge. Alternatively, the second mechanism can form part of the base.

The control unit can form part of the cartridge, or preferably of the base.

The actuator element can form part of the cartridge, or preferably of the base.

Non-limitatively, the second closure mechanism can be in closed position when it is idle, i.e. when no force is applied thereto. Thus, when idle no drug can be delivered. When the second mechanism is actuated, for example by the management unit, it can pass into the open position, thus allowing the passage of a drug.

According to an embodiment example that is in no way limitative, the second mechanism can comprise at least one shutter, in particular a double shutter forming a jaw. In the idle state, said at least one shutter (or said jaw) is closed and opposes the passage of the drug. When the first mechanism is actuated, said at least one shutter (or said jaw) moves away and allows the passage of (a) drug(s).

According to embodiments, the second mechanism can open and close in a plane perpendicular to the direction of passage of the drug.

In the event that the device is used for dispensing drugs in the form of capsules (or tablets), said device can comprise a means for delivery of said drugs in single units, i.e. a means ensuring the delivery of a single capsule (or a single tablet) at a time.

The means for delivery of drugs in single units can be displaced between:

an open position allowing the passage of the next capsule to be delivered, in particular when no capsule is in the process of being delivered; and a closed position preventing the passage of a capsule (or a tablet) following the capsule that is in the process of being delivered.

Such a means can comprise a shutter, and in particular a double shutter forming a jaw, which can be displaced between an open position and a closed position, arranged upstream of the dispensing opening, for example on a duct connecting the container to said dispensing opening.

In particular, in the idle state, the shutter(s) can be in the open position and pass to the closed position under the action of the user, for example by a press on the device.

According to embodiments, the first mechanism and the single-unit delivery means can be coupled so that they can be actuated simultaneously, in particular by the user. In other words, the single-unit delivery means can be incorporated with/in the first mechanism.

For example, the at least one shutter of the first mechanism and the at least one shutter of the single-unit delivery means can be arranged on one and the same moveable part, such as a rotary arm. Thus, by actuating said arm, it is possible to actuate the first mechanism and the single-unit delivery means at the same time.

According to an architecture that is in no way limitative, the container can be formed by a cover assembled with the rest of said device.

In particular, the cover can be assembled with the rest of the device in an upper part of said device, and/or in a part of the device opposite the dispensing opening.

The cover can be assembled with the rest of the device so that it cannot be removed, or detached, from the rest of the device without damaging said device or said cover. Thus, when the cover is assembled with the rest of the device it is no longer possible to gain access, or to handle the drugs present in the container.

Preferably, the container is designed and provided to receive loose drugs. In particular, when the device is used for dispensing a drug in the form of capsules or tablets, the capsules or tablets are arranged loose in the container.

The cover can be assembled with the rest of the device by clipping, bonding, screwing, etc.

According to embodiments, the container can comprise a sensor of the opening of said container.

In particular, when the container is formed by a cover assembled with the rest of the device, then the opening sensor can be arranged at the level of the line of assembly of said cover with the rest of the device.

According to an embodiment example, the opening sensor can be a passive sensor that is damaged when the cover is moved or detached, at least partially, from the rest of the device.

The device according to the invention can moreover comprise a management unit configured to allow, or not, dispensing of the drug to the user.

Allowing dispensing or not can be carried out as a function of:

the operational state of at least one degradable sensor, and/or at least one data item measured by at least one non-degradable sensor, and/or at least one data item stored in the electronic chip, and/or at least one predefined condition applicable to said data item.

The at least one tested data item can be any one of the data items listed above.

At least one condition can be a comparison of at least one data item with at least one predefined reference data item or threshold value.

Preferably, but in no way limitatively, at least one condition can be tested before the first dispensing of the drug, or before each dispensing of the drug.

At least one reference data item, respectively at least one threshold value, can be stored beforehand in the management unit.

Alternatively, or in addition, at least one reference data item, respectively at least one threshold value, can be loaded from a remote site. Loading can be carried out before the first dispensing of a drug, or before each dispensing of a drug.

The management unit can be a processor or a calculation unit, or a computer chip, optionally loaded with a computer program, configured to carry out the operations described above.

According to versions, the device according to the invention can be presented in the form of a cartridge forming said container for a drug, and provided to be used in an appliance for dispensing a drug.

Such an appliance can comprise at least one site provided to receive, in particular interchangeably, a device according to the invention.

In particular, such an appliance can be presented in the form of a base, or a stand, provided to receive, in particular interchangeably, a device according to the invention.

In this case, releasing the dispensing opening of the device according to the invention can advantageously be carried out when the device according to the invention is coupled, or engaged, with the dispensing appliance. For example, such a coupling can tear a lid covering the dispensing opening.

According to versions, the device according to the invention can be presented in the form of an appliance for dispensing a drug comprising:

- the container, and
- at least one part forming a base to said container, and cooperating with said container for dispensing a drug present in said container.

In this case, the at least one of the components described above can be located in the base of the device. In particular, the base can comprise any combination of at least one of the following elements:

- at least one sensor,
- the biometric reader,
- the communication module,
- the quantification module,
- the closure module, and
- the management unit.

In the version where the device is presented in the form of an appliance comprising a container and a base, said container can be fixed to, or incorporated in, the base in a non-interchangeable manner.

In this case, the container forms an integral part of the dispensing appliance and cannot be separated from the base.

In this embodiment, the electronic chip can be arranged at the level of the container, or at the level of the base.

In the version where the device according to the invention is presented in the form of an appliance comprising a container and a base, the container can alternatively be removably coupled to the base such that said base can interchangeably receive a container from among several containers.

In this case, the container can be defined in, or be presented in the form of, a removable cartridge such as described above.

In this case, the chip is preferably arranged in, or on, the container.

In this case, the base is reusable with different containers comprising identical or different drugs.

According to another aspect of the present invention, a system for dispensing a drug is proposed comprising:

- a central server, and
- at least one device for dispensing a drug according to the invention, in communication with said central server.

At least one dispensing device can be in communication with the remote server through a wired or wireless communication.

At least one dispensing device can be in communication with the remote server through a communication network, such as the Internet.

Thus, at least one communication device can load, from or to the remote server, at least one data item relating to dispensing a drug, such as at least one condition/data item to be tested in order to dispense a drug or a data item relating to the applicable dosage. Thus, it is possible to modify dynamically, remotely on the fly, data items relating to dispensing a drug, such as for example a dosage. It is possible to stop or start taking of a drug dynamically, remotely on the fly. It is also possible to lock the dispensing based on an indicator showing that the drug is unsuitable for use, such as for example exceeding its expiry date, a value for exposure to an unduly extreme temperature, an invalid authentication certificate. All these characteristics allow improved control of the dispensing of a drug to a user.

BRIEF DESCRIPTION OF THE DRAWINGS

Other advantages and characteristics will become apparent on examining the detailed description of embodiments which are in no way limitative, and from the attached drawings, in which.

DETAILED DESCRIPTION

It is well understood that the embodiments that will be described hereinafter are in no way limitative. Variants of the invention can in particular be envisaged comprising only a selection of the characteristics described hereinafter, in isolation from the other characteristics described, if this selection of characteristics is sufficient to confer a technical advantage or to differentiate the invention with respect to the state of the prior art. This selection comprises at least one, preferably functional, characteristic without structural details, or with only a part of the structural details if this part alone is sufficient to confer a technical advantage or to differentiate the invention with respect to the state of the prior art.

In particular, all the variants and all the embodiments described can be combined together if there is no objection to this combination from a technical point of view.

In the figures and in the rest of the description, the elements common to several figures retain the same reference.

Figure 1:
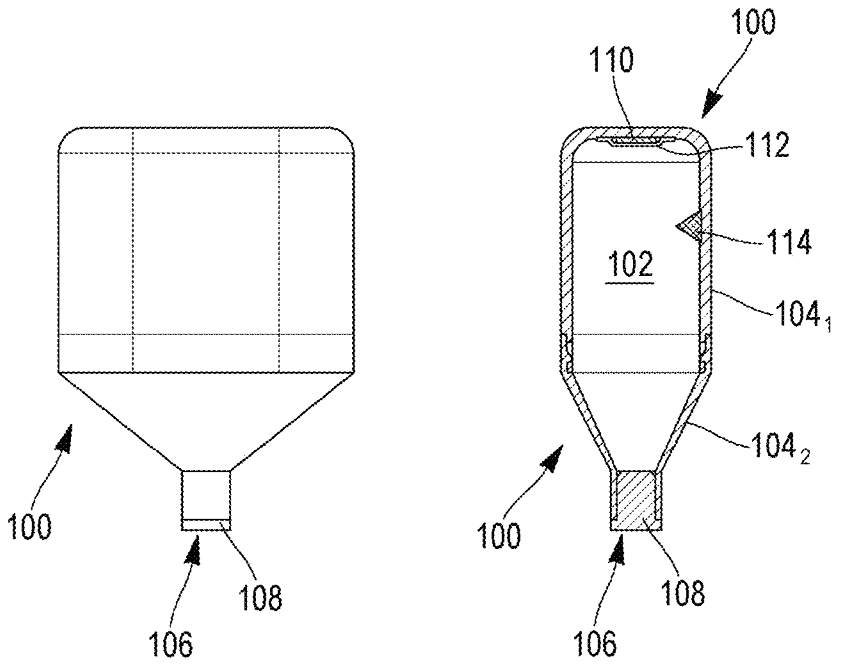
FIGS. 1-2 are diagrammatic representations of embodiment examples of a device for dispensing a drug according to the invention, in particular when said device is presented in the form of a cartridge that can be adapted to a stand.

FIG. 1 is a diagrammatic representation of a non-limitative embodiment example of a device for dispensing a drug, in a side view and in a cross section view.

The device 100 in FIG. 1 is presented in the form of a cartridge provided to adapt and to be coupled to an appliance, or a base, for dispensing a drug, and in particular removably and in particular interchangeably with other similar or identical devices.

The device 100 comprises a container 102 for receiving a drug that is gaseous, liquid or solid (in the form of a powder or capsules). Preferably, the container 102 is closed, in particular in a watertight manner and in particular in an airtight manner. In the example shown, the device 100 is formed by two parts 1041 and 1042 assembled together, for example by welding, screwing or by bonding, after filling said container 102 with a drug (not shown).

The container 102 is connected to a dispensing opening 106 making it possible for the drug present in the container 102 to exit said container 102. In the example shown, the drug exits the container by the effect of gravity, since in the configuration of use the dispensing opening 106 is located downwards.

The dispensing opening 106 is closed and protected by a lid 108, in particular in a watertight manner and in particular in an airtight manner. This lid 108 makes it possible to protect the drug present in the container 102 during transport and storage of the device 100. The lid 108 is provided to be perforated during first use of the device 100, for example by coupling the device with an appliance or a stand for dispensing drugs.

Advantageously, the device 100 comprises a sensor 110, sensitive to at least one physical quantity, and making it possible to determine if the drug present in the container has been degraded or not.

In the example in FIG. 1, the sensor 110 is arranged inside the container 102. In particular, the sensor 110 is arranged on an inner face of a base wall of the container opposite to the dispensing opening 108.

The sensor 110 is bonded on the wall of the container 102.

The sensor 110 is covered with a watertight and/or airtight coating 112 to protect said electronic chip 110, in particular with respect to the drug present in the container, and vice versa.

The sensor 110 can be a standard sensor for measuring the value of one or more physical quantities and communicating the measured values to an external appliance, or to a memory (not shown) or an electronic chip (not shown) of the device 100.

The sensor 110 can be a sensor that degrades when the value of at least one physical quantity to which it is sensitive reaches a maximum threshold value and/or a minimum threshold value.

In the example shown, the sensor 110 is a passive RFID tag comprising an electronic chip and a communication antenna, and is designed to be degraded when the value of at least one physical quantity to which it is sensitive reaches a maximum threshold value and/or a minimum threshold value. The electronic chip can store an identification data item of the device 100.

Thus, provided that the value of at least one physical quantity to which the tag 110 is sensitive has not reached a maximum threshold value and/or a minimum threshold value, said tag can be read by a reader. Otherwise, the RFID tag cannot be read by a reader: the drug present in the container is potentially degraded and must not be dispensed to a user.

The sensor 110 can be sensitive to one or more of the following quantities: temperature, hygrometry, luminosity, radiation, pressure, shock, vibration, etc. acting on said container.

Optionally, the device 100 can comprise at least one other sensor, namely a sensor 114, for measuring the value of at least one physical quantity. At least one value measured by the at least one sensor 114 can be communicated to an appliance external to the device 100, or to an electronic chip or a memory of said device, for storage. Such an electronic chip (or such a memory) can be the RFID tag 110, or also an electronic chip (or a memory) other than the RFID tag.

In the example shown diagrammatically and non-limitatively, the sensor 114 is arranged on an inner face of the container 102.

In the example shown diagrammatically and non-limitatively, a single sensor 114 is shown. The device 100 can comprise several sensors 114, each sensitive to one or more physical quantities.

Generally, the device 100 can comprise any combination of at least one of the following sensors:

- at least one position sensor, such as a GPS sensor, for measuring at least one location data item of said device;
- at least one sensor of a physical parameter relating to said container, such as a sensor of the temperature within the container, a sensor of hygrometry within the container, a sensor of light entering the container, at least one sensor of a radiation propagating in said container, at least one sensor of pressure within the container, at least one sensor of shock acting on said container such as an accelerometer, at least one sensor of vibration of said container, and more generally a sensor for measuring any physical parameter capable of affecting the drug present in the container 102;
- at least one sensor monitoring the state of release or not of the dispensing opening, i.e. the state of the lid 108.

Figure 2:
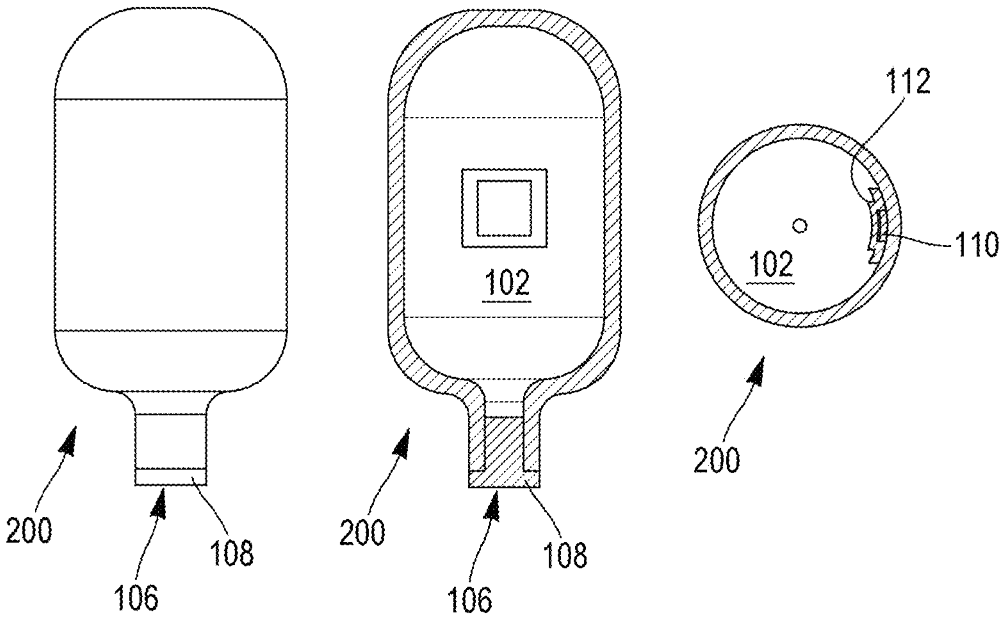

FIG. 2 is a diagrammatic representation of a non-limitative embodiment example of another device for dispensing drugs, in side view and two cross section views.

The device 200 in FIG. 2 is presented in the form of a cartridge provided to adapt and to be coupled to an appliance, or a base, for dispensing a drug, and in particular removably and in particular interchangeably with at least one other similar or identical device for dispensing a drug.

The device 200 in FIG. 2 comprises all the elements of the device 100 in FIG. 1, save with respect to the differences mentioned below.

Unlike the device 100, in the device 200, the container 102 is produced in a single piece, for example by moulding or by machining. In this case, the container 102 can be filled via the dispensing opening 106. Then, the dispensing opening 106 can be closed by means of the lid 108.

In addition, unlike the device 100, in the device 200, the sensor 110 is arranged on an inner face of a side wall of the container 102. This embodiment can in particular be used when the drug is not in a liquid form.

Moreover, the device 200 does not comprise a sensor 114.

Each of the devices 100 and 200 can be produced from any material compatible with the drug that is present in the container, such as from plastic, metal, resin, cardboard, rubber, glass or wood, etc.

Figure 3:
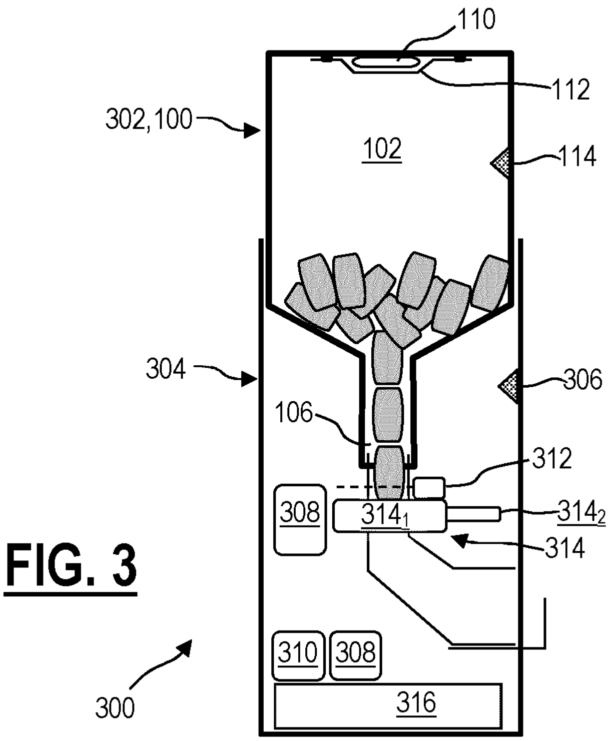
FIGS. 3-4 are diagrammatic representations of embodiment examples of a device for dispensing a drug according to the invention, in particular when said device is presented in the form of an appliance for dispensing a drug.

FIG. 3 is a diagrammatic representation of another non-limitative embodiment example of a device for dispensing a drug according to the invention, in particular when said device is presented in the form of an appliance for dispensing a drug.

The device 300 shown in FIG. 3 comprises a cartridge 302 comprising a container 102, an electronic chip 110 arranged in the container 102 and an opening 106 for dispensing a drug to outside said container, in particular under the effect of gravity. The cartridge 302 can be any one of the devices 100 or 200 in FIGS. 1 and 2. In the example in FIG. 3, the cartridge 302 corresponds to the device 100 in FIG. 1 and thus comprises all the elements of this device.

In the example in FIG. 3, the cartridge 302 is coupled to a base 304, in particular removably such that the base 304 can receive interchangeably, and one at a time, several cartridges identical or similar to the cartridge 302.

Perforating the lid, or the membrane, protecting the dispensing opening 106 can be carried out, in particular automatically or simultaneously, when the cartridge 302 is inserted into the base 304.

The base 304 comprises a power supply (not shown), wired or via battery, for the different optional components of the device 300 that will now be described.

Generally, the device according to the invention comprises at least one sensor, each sensor being sensitive to at least one physical quantity within said container capable of affecting the integrity of the drug present in said container, such as for example the sensors 110 and 114, arranged in the container 102. In the example shown, the device 300 comprises the sensor 110 and the sensor 114, each arranged in the container. Alternatively, the device 300 can comprise only one of the sensors 110 and 114.

The device 300 can comprise, in addition to the sensors 110 and 114, one or more sensors 306, arranged at the level of the base 304, for measuring the value of at least one parameter relating to the drug, and/or to said cartridge, and/or to the stand. The measured value can be stored locally in a memory of said device, or remotely, for example in a remote server.

In the example shown diagrammatically and non-limitatively, a single sensor 306 is shown arranged in the stand 304. Generally, the or each sensor 306 can be any one of the following sensors:

- at least one position sensor, such as a GPS sensor, for measuring at least one location data item of the device 300;
- at least one sensor of a physical parameter relating to said device, such as a temperature sensor, a hygrometry sensor, a light sensor, a radiation sensor, a pressure sensor, a shock sensor, a vibration sensor, etc.

Optionally, the device 300 can comprise a reader of biometric data items, such as a fingerprint reader 308, for identifying the user. Thus, before at least one, in particular each, dispensing of a drug, it is possible to verify the identity of the user to whom the drug is delivered, which makes it possible to avoid errors concerning the user for whom the drug is intended, or a misappropriation of the drug for a use other than the drug being taken by the intended patient (resale, drug misuse, suicide, self-medication, etc.). The identity of the user entitled to the final dispensing of the prescribed drug(s) can be determined by comparing the measured biometric data item with a reference biometric data item measured and stored beforehand, either locally or remotely. In the latter case, the biometric data item can be loaded from the remote site.

The at least one biometric reader can be arranged on the container 302. Alternatively, as shown in FIG. 3, the biometric reader 308 can be arranged in, or on, the stand 304.

Optionally, but advantageously, the device 300 can comprise a communication module 310, wired or wireless, for example via a network of the internet type, with a remote server (not shown in FIG. 3). Such a communication module makes it possible to send and/or receive data items relating to the drug, and/or data items relating to the cartridge 302, and/or data items relating to the device 300, and/or data items relating to the user, and/or data items relating to the dosage.

The communication module 310 can for example transmit data items relating to the identity of the device 300, or of a user of said device, to the remote site in order to obtain data items relating to dispensing the drug present in the container. These data items can comprise one or more conditions to be verified in order to dispense the drug, data items of dosage of the drug, etc.

The communication module 310 can be arranged on, or in, the container 302. Alternatively, as shown in FIG. 3, the communication module 310 can be arranged in, or on, the stand 304.

Optionally, but particularly advantageously, the device 300 can comprise a sensor 312 of a quantity of a drug exiting the container 102 via the dispensing opening 106.

Such a sensor makes it possible to ensure that the quantity of the drug dispensed is in accordance with the dosage associated with a user.

Such a sensor 312 can be any type of mechanical, electrical, optical sensor. In the example shown, the sensor 312 is an optical sensor making it possible to count the number of capsules exiting the container 102.

The sensor 312 can be arranged on, or in, the container. Alternatively, as shown in FIG. 3, the sensor 312 is arranged in, or on, the stand 304, downstream of the dispensing opening 106.

Optionally, but particularly advantageously, the device 300 can comprise a closure means 314, arranged downstream of the dispensing opening 106, which can be displaced between a first position allowing the passage of the drugs and a second position preventing the passage of the drugs.

The closure means 314 comprises a controllable actuator $\mathbf{314}_1$ provided to displace a member $\mathbf{314}_2$ forming a physical obstacle to the passage of the drug, in the second position. The member $\mathbf{314}_2$ forming a physical obstacle can be a tab, a mask, a cover, or any other object opposing the passage of the drug. The actuator $\mathbf{314}_1$ can be a motor, or a cylinder, or also a magnetic actuator, or any other actuator capable of being controlled by an electrical signal, or a wave, and displacing the member $\mathbf{314}_2$.

The closure means 314 can be controllable, for example by a management unit of the device 300 such that, when an abnormality is detected, said closure means 314 is positioned in its second position. An abnormality can be associated with any one of the data items or parameters described above.

The closure means 314 can be arranged on, or in, the container. Alternatively, as shown in FIG. 3, the closure means 314 is arranged in, or on, the stand 304, downstream of the dispensing opening 106.

Optionally, but particularly advantageously, the device 300 comprises a management unit 316 configured to allow, or not, dispensing of the drug to the user as a function of at least one data item stored in the electronic chip 110 and of at least one predefined condition.

The management unit 316 can be a processor configured by a computer program.

The management unit 316 can be arranged on, or in, the container. Alternatively, as shown in FIG. 3, the management unit 316 is arranged in, or on, the stand 304.

For example, the management unit can be configured to carry out any combination of at least one of the following operations:

- polling a degradable sensor, such as the sensor 110, to determine its operational state;
- comparing a temperature data item, and/or a pressure data item, and/or a hygrometry data item, etc., for example measured by the sensor 114, with at least one threshold value stored locally or loaded from a remote site;
- comparing a biometric data item read by the biometric reader to a reference biometric data item, stored locally or loaded from a remote site;
- controlling the closure means as a function of at least one quantity data item measured by the sensor 312 and at least one dosage data item stored locally or loaded from a remote site,
- etc.

Of course, the device 300 can comprise components other than those that have just been described. For example, the device 300 can comprise:

- at least one battery supplying said device, or an interface of a wired supply;
- at least one computer memory,
- at least one display screen, touch-sensitive or not,
- etc.

Figure 4:
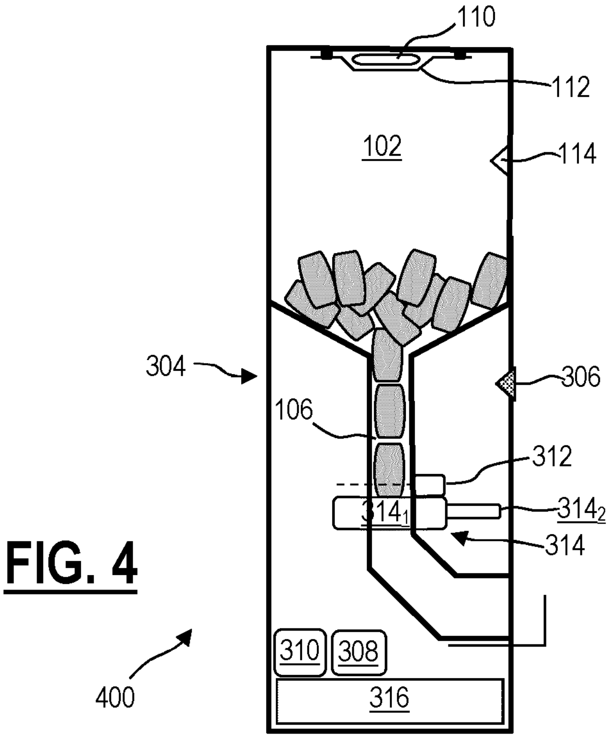

FIG. 4 is a diagrammatic representation of another non-limitative embodiment example of a device for dispensing a drug according to the invention, in particular when said device is presented in the form of an appliance for dispensing a drug.

The device 400 in FIG. 4 comprises all the elements of the device 300 in FIG. 3, save with respect to the differences mentioned below.

In the example in FIG. 4, unlike the device 300, the container 102 is incorporated in the device 400 and is not formed by a removable cartridge 302. In other words, in the device 400, the container is not removable.

Figure 5:
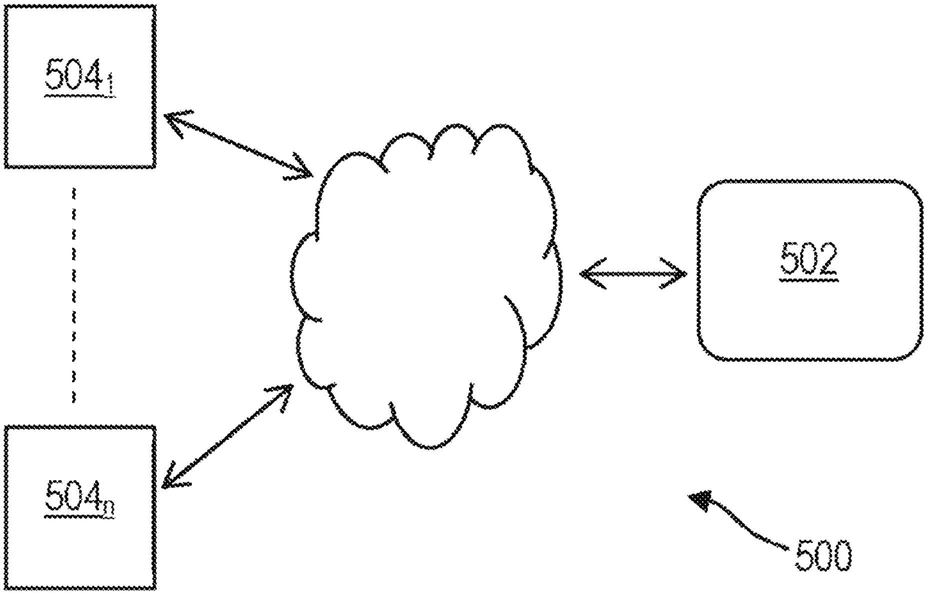
FIG. 5 is a representation of an embodiment example of a system according to the invention.

FIG. 5 is a diagrammatic representation of a non-limitative embodiment example of a system for dispensing a drug according to the invention.

The system 500 in FIG. 5 comprises a central server 502 to which is connected a plurality of dispensing devices $504_1$-$504_n$, via a communication network 506 of the internet type. The central server is located for example on a site remote from each of the devices $504_1$-$504_n$.

At least one of the dispensing devices $504_1$-$504_n$ can be any one of the devices 100 or 200 in FIG. 1 or 2, or the device 600 in FIGS. **6*a*-6*e***. In this case, each dispensing device is coupled with a dispensing appliance, or a stand, itself connected to said internetwork.

At least one of the dispensing devices $504_1$-$504_n$ can be any one of the devices 300 or 400 in FIG. 1 or 2. In this case, each dispensing device is itself connected to said internetwork, optionally via a connecting gateway.

FIGS. **6*a*-6*e*** are diagrammatic representations of another non-limitative embodiment example of a device for dispensing a drug according to the invention.

The device 600 in FIGS. **6*a*-6*e*** is presented in the form of a cartridge provided to be used with an appliance, or a base, for dispensing a drug, and in particular removably and in particular interchangeably.

Figure 6A:
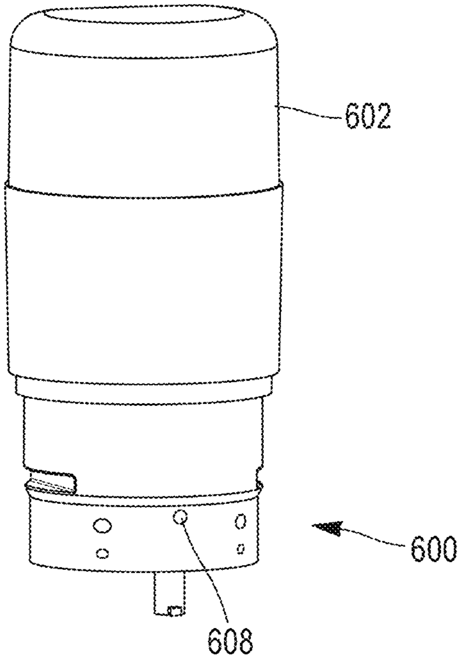
FIGS. 6*a* to 6*e* are diagrammatic representations of another non-limitative embodiment example of a device according to the invention.
Figure 6B:
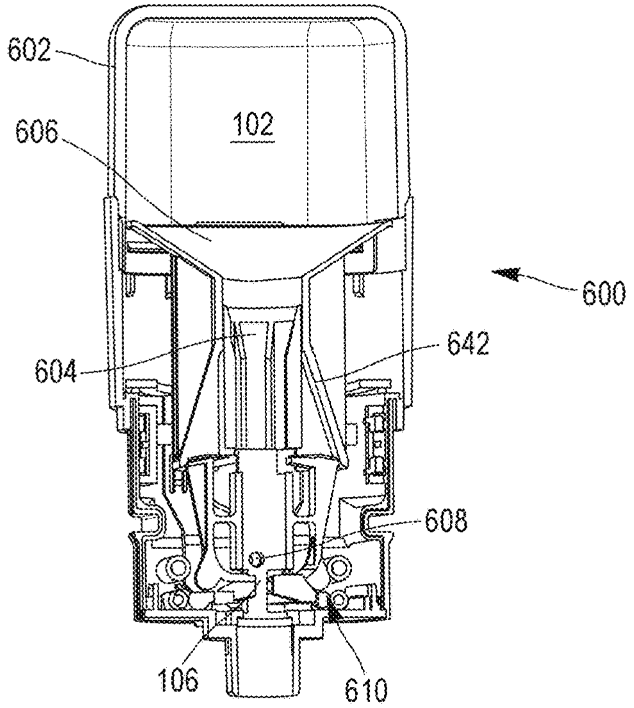
Figure 6C:
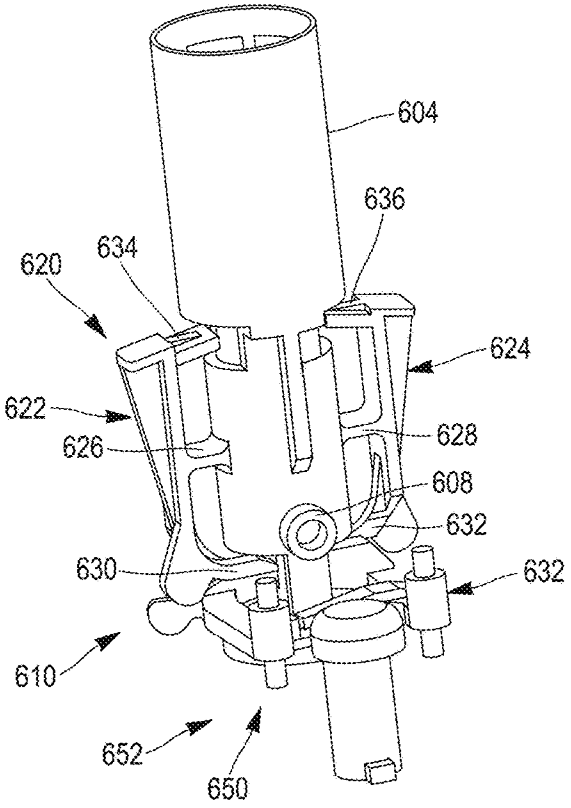
Figure 6D:
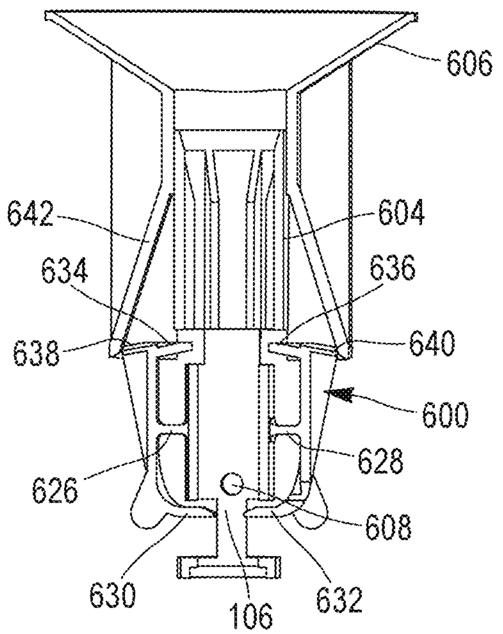
Figure 6E:
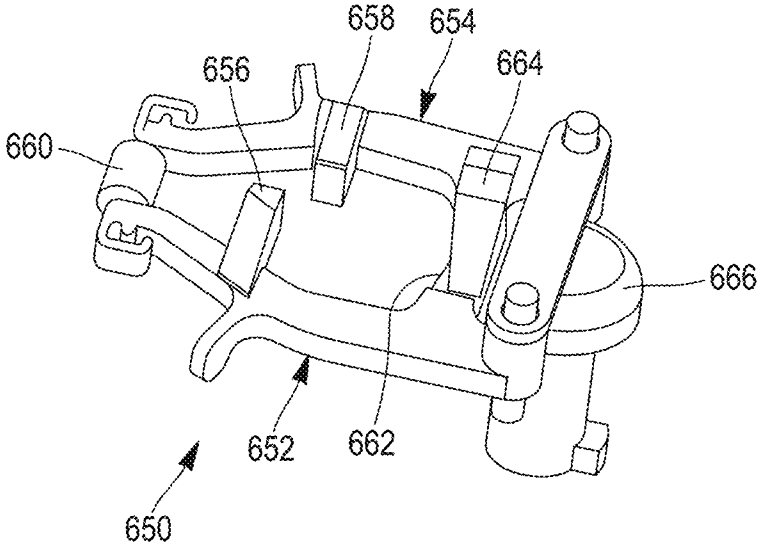

The device 600 is shown in FIG. **6*a* in a side view, in FIG. 6*b* in a vertical section view. FIGS. 6*c*-6*e* show the closure means equipping the device 600**.

As shown in FIGS. **6*a* and 6*b*, the device 600 is presented in the form of a cartridge, in particular longitudinal, provided to be coupled to a base, for dispensing a drug. In particular, the device 600** is used for dispensing drugs in the form of capsules or tablets. In the description hereinafter, the term "capsule" denotes a solid single-unit form of a drug, such as a capsule or a tablet.

The device 600 comprises a container 102 provided in the upper part of the device 600. The container 102 is formed by a cover 602, presented in the form of a cup or beaker, assembled with the rest of the device 600 for example by clipping. Thus, the cover 602 can be filled with capsules to be distributed then assembled with the rest of the device 600, which facilitates both filling the container 102 and also the manufacture of the device 600.

The device 600 comprises a duct 604, called conveying duct 604, for conveying a capsule present in the container 102 to the dispensing opening 106, for its delivery to the user. The duct 604 communicates with the container 102, in its upper part, by virtue of a part 606, in the form of a funnel, for assisting the passage of the drugs present in the container 102 to said duct 604. In addition, the width of the duct 604 is dimensioned such that the capsules are conveyed one after another in said conveying duct 604. Each capsule that passes through the conveying duct 604 falls by gravity towards the dispensing opening 106.

The device 600 comprises a radial opening 608, provided on the duct 604 for detecting each capsule conveyed through said duct 604, and optionally for counting the number of capsules dispensed.

The device 600 comprises a sensor, such as the sensor 110, sensitive to at least one physical quantity, and making it possible to determine if the drug present in the container has been degraded or not, arranged in the container, as described above. The device 600 can moreover comprise any combination of the sensors described above with reference to the devices 100-400, and which are not repeated here for reasons of brevity.

The device 600 comprises moreover a closure means 610 for controlling the dispensing of capsules. The closure means 610 can be seen more clearly in FIG. **6*c***.

In the device 600, the closure means 610 comprises, particularly advantageously, two closure mechanisms operating independently of one another.

In this example, the closure means 610 comprises a first closure mechanism 620, which can be displaced between an open position allowing the passage of a drug and a closed position preventing the passage of a drug.

According to embodiments, the first closure mechanism 620 is provided to be actuated by the user.

The first closure mechanism 620, which can be seen in FIG. **6*c*, is also shown in cross section view in 6*d*, mounted on the conveying duct 604**.

In the non-limitative example, the first closure mechanism 620 comprises two arms 622 and 624 positioned on one side and on the other side of the duct 604, and extending substantially in the direction of said duct 604. Each arm 622 and 624 is fastened on the duct 604 by a flexible securing bracket, respectively 626 and 628, making it possible for said arm 622 and 624 to be displaced about an axis of rotation perpendicular to the direction of passage of the drugs, or perpendicular to said conveying duct 604. Each of the securing brackets 626 and 628 thus makes it possible to pivot the corresponding arm 622 or 624.

Each arm 622 and 624 contains, in its lower part, a shutter presented in the form of a tooth or a hook, respectively 630 and 632, extending towards the other one of the arms such that the arms 622 and 624 with their shutter 630 and 632 form a jaw, called downstream jaw, downstream of the dispensing opening 106.

In addition, each arm 622 and 624 contains, in its upper part, a shutter presented in the form of a tooth or a hook, respectively 634 and 636, extending towards the other one of the arms such that the arms 622 and 624 with their shutter 634 and 636 form a jaw, called upstream jaw, upstream of the dispensing opening 106. When the arms 622 and 624 are pivoted in a first direction with respect to the duct 604, the shutters 634 and 636 are thrust into the duct 604 via radial openings arranged in said duct facing these shutters, leading to closing of the duct 604 by the upstream jaw. When the arms 622 and 624 are pivoted in a second direction with respect to the duct 604, the shutters 630 and 632 are thrust into the duct 604 via other radial openings arranged in the duct facing these shutters, leading to closing of the duct 604 by the downstream jaw.

Advantageously, the distance between the downstream jaw and the upstream jaw of the first mechanism is chosen such that it is slightly greater than the length of a capsule in the direction of the duct 604. In other words, in the situation of use, a single capsule can be located between the downstream and upstream jaws.

Moreover, each arm 622 and 624 contains, in its upper part, a shoulder, respectively 638 and 640, extending radially outwards with respect to the duct 604, provided to be subjected to a pressing force so as to pivot said arm 622 and 624, in particular in said first direction.

In the example shown, and without loss of generality, the part 606 contains an inclined peripheral wall 642, in the form of an inverted funnel, which presses on the two arms 622 and 624 so as to exert said pressing force under the action of a press by the user.

When idle, the downstream jaw formed by the shutters 630 and 632 is closed and the upstream jaw formed by the shutters 634 and 636 is open. Thus, a capsule can pass into the conveying duct 604 and be positioned between the upstream and downstream jaws. As the downstream jaw is closed, the capsule cannot exit the conveying duct 604 and remains between the upstream and downstream jaws. When the user applies a pressure on the device 600, in the longitudinal direction of said device 600, the part 606 is displaced along the duct 604, and the inclined wall 642 presses on the shoulders 638 and 640 such that the arms 622 and 624 are displaced in rotation. The shutters 630 and 632 move apart such that the downstream jaw opens. At the same time, the shutters 634 and 636 move towards one another such that the upstream jaw closes. The capsule present between the jaws is then released and allowed to exit the duct. As the upstream jaw is closed, no other capsule can exit. When the user releases the pressure, the arms 622 and 624 return to their idle position in which the downstream jaw is closed and the upstream jaw is open. A new capsule is introduced between said jaws, and so on and so forth.

Thus, the first mechanism 620 allows a controlled, single-unit dispensing of a drug.

In this example, the closure means 610 comprises a second closure mechanism 650, which can be displaced between an open position allowing the passage of capsules and a closed position preventing the passage of capsules.

The second closure mechanism 650, shown in FIG. 6*c*, is also shown in FIG. 6*e* in a perspective top view, separately from the rest of the device 600 for greater clarity.

In the non-limitative example, the second closure mechanism 650 extends in a plane perpendicular to the duct 604, below the dispensing opening 106, and in particular below the first closure mechanism.

In the non-limitative example, the second closure mechanism 650 comprises two arms 652 and 654 positioned on one side and on the other side of the duct 604, and extending substantially in a direction perpendicular to the duct 604.

Each arm 652 and 654 contains a shutter presented in the form of a tooth or a hook, respectively 656 and 658, extending towards the other one of the arms such that the arms 652 and 654 with their shutter 656 and 658 form a jaw, downstream of the dispensing opening 106, and in particular downstream of the first closure mechanism.

The arms 652 and 654 are mounted in rotation about a pivot at a first end, and connected together by a spring 660 at the opposite end.

Moreover, each arm 652 and 654 contains, on the side of its first end, a shoulder, respectively 662 and 664, provided to be subjected to a pressing force so as to displace said arm 622 and 624, in particular in rotation about its pivot, and move it away from the other one of the arms.

In the example shown, and without loss of generality, a member 666 is provided to cooperate with the two shoulders 662 and 664 so as to exert said pressing force. This member 666 comprises a head forming a cam making it possible to exert the pressing force selectively as a function of the position of the member 666 about an axis of rotation of this member 666, this axis of rotation being in this example parallel to the direction of the duct 604.

When idle, the jaw formed by the shutters 656 and 658 is closed. No capsule can be dispensed to the user. When the member 666 is displaced about its axis of rotation, its head pushes back the arms 662 and 664, and thus causes the jaw to open, thus allowing the capsule(s) to pass.

The second mechanism can be controlled by a management unit of said device, for example according to at least one tested data item/condition, such as one of, or any combination of at least two of, the data items/conditions listed above.

The management unit can be arranged in the device 600.

Alternatively, the management unit can be arranged in a base (not shown in FIGS. 6*a*-6*e*) with which the device is intended to be used, such as for example the base 304. In this case, the management unit can control the second mechanism by virtue of an actuator (not shown), such as a motor or a cylinder, for actuating the member 666. The actuator can be arranged in the base.

Thus, in the device 600 the drug is dispensed in single units. In addition, dispensing of the drug is subject to:

a user action, in particular for actuating the first closure mechanism 620; and an action of the management unit, in particular for actuating the second closure mechanism 650.

Thus, dispensing the drug can be subject on the one hand to the presence and to the action of the user, but also to one or more verification(s), carried out by the management unit.

Of course, the example given in FIGS. 6*a*-6*e* is in no way limitative.

The first and the second mechanism can present forms other than those described. For example, it is possible for the first mechanism to comprise only a single jaw, namely the downstream jaw.

In addition, the device can comprise a single one of the first and second mechanisms. For example, the device can comprise only the first mechanism or the second mechanism.

Figure 7:
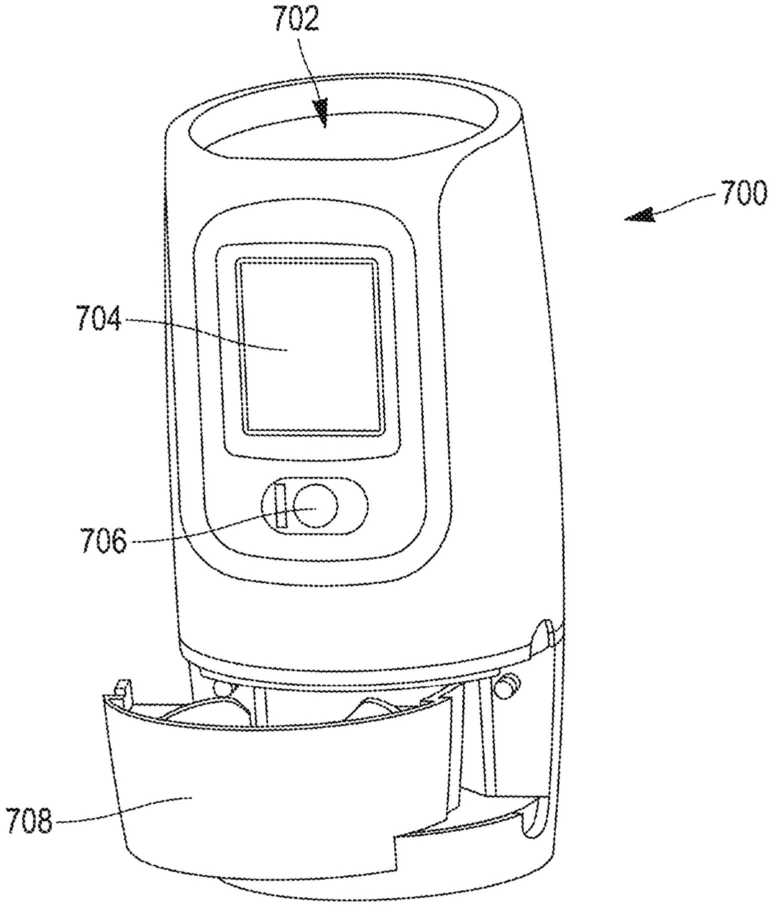
FIG. 7 is a diagrammatic representation of a non-limitative embodiment example of a base with which a device according to the invention can be used, when it is presented in the form of a cartridge.

FIG. 7 is a diagrammatic representation of a non-limitative embodiment example of a base with which a device according to the invention can be used, when it is presented in the form of a cartridge.

The base 700 in FIG. 7 can be the base 304 in FIG. 3 or 4.

The base 700 can be used with any one of the cartridges 100, 200, 302 and 600.

The base 700 comprises, in its upper part, an opening 702 for receiving a cartridge, such as for example the cartridge 600. The lower part of the cartridge 600 is introduced into the base 700 in the configuration of use.

The base 700 comprises a display screen 704, a fingerprint reader 706, a management unit, at least one battery, in particular a rechargeable battery, optionally an actuator for actuating the second closure mechanism, optionally a communication module, etc. such as described above.

The base 700 moreover comprises a receptacle 708, presented in the form of a drawer, for collecting the dispensed drugs.

Of course, the invention is not limited to the examples that have just been described.

The invention claimed is:

1. A device for packaging, transporting and/or dispensing drugs comprising:

a closed container for a drug, provided to receive at least one drug to be dispensed and comprising an opening for dispensing a drug, intended to be released when a drug is dispensed;

at least one sensor, sensitive to at least one physical quantity within said container and said at least one physical quantity capable of affecting the integrity of said at least one drug present in said container; and:

said at least one sensor degrades when the value of said at least one physical quantity exceeds a threshold value; or is a passive RFID tag, comprising a chip and an antenna, and which can no longer be read when the value of at least one physical quantity exceeds a threshold value.

2. The device according to claim 1, characterized in that at least one said sensor is arranged in the container.

3. The device according to claim 1, characterized in that at least one said sensor is arranged in a housing provided in said container.

4. The device according to claim 1, further including an electronic chip for storing:

at least one data item relating to the at least one drug present in said container, at least one data item relating to a user, and/or at least one data item relating to a dosage.

5. The device according to claim 1, further including at least one of:

at least one biometric reader for reading at least one biometric data item of a user;

a module for communicating with a remote site, via a connection, wired or not, for sending and/or receiving data items;

a module for measuring a quantity of a drug exiting the container via the dispensing opening; and a management unit configured to allow, or not, dispensing of the drug to the user as a function of at least one data item stored in the electronic chip and of at least one predefined condition applicable to said data item.

6. The device according to claim 1, further including a closure means that can be displaced between a first position allowing the passage of a drug through the dispensing opening and a second position preventing the passage of a drug through the dispensing opening.

7. The device according to claim 6, characterized in that the closure means comprises a first mechanism, which can be displaced between an open position allowing the passage of a drug through the dispensing opening and a closed position preventing the passage of a drug through the dispensing opening, and provided to be actuated by the user.

8. The device according to claim 6, characterized in that the closure means comprises a second mechanism, which can be displaced between an open position allowing the passage of a drug and a closed position preventing the passage of a drug, and provided to be actuated automatically.

9. The device according to claim 1, characterized in that the container is formed by a cover assembled with the rest of said device.

10. The device according to claim 1, characterized in that the device is presented in the form of a cartridge forming said container for a drug, and provided to be used in an appliance for dispensing a drug.

11. The device according to claim 1, characterized in that the device is presented in the form of an appliance for dispensing a drug comprising:

the container; and at least one part forming a base to said container, and cooperating with said container for dispensing a drug present in said container.

12. The device according to claim 11, characterized in that the container is removably coupled to the base such that said base can interchangeably receive a container from among several containers.

13. A system for dispensing a drug comprising:

a central server; and at least one device for dispensing a drug according to claim 1, in communication with said central server.

14. A device for packaging, transporting and/or dispensing drugs comprising:

a closed container for a drug, provided to receive at least one drug to be dispensed and comprising an opening for dispensing a drug, intended to be released when a drug is dispensed;

at least one sensor, sensitive to at least one physical quantity within said container and said at least one physical quantity capable of affecting the integrity of said at least one drug present in said container; and said at least one sensor degrades when the value of said at least one physical quantity exceeds a threshold value.

15. The device according to claim 14, characterized in that at least one said sensor is arranged in the container.

16. The device according to claim 14, characterized in that at least one said sensor is arranged in a housing provided in said container.

17. The device according to claim 14, characterized in that said at least one sensor is a passive RFID tag, comprising a chip and an antenna, and which can no longer be read when the value of at least one physical quantity exceeds a threshold value.

18. A device for packaging, transporting and/or dispensing drugs comprising:

a closed container for a drug, provided to receive at least one drug to be dispensed and comprising an opening for dispensing a drug, intended to be released when a drug is dispensed;

at least one sensor, sensitive to at least one physical quantity within said container and said at least one physical quantity capable of affecting the integrity of said at least one drug present in said container; and said at least one sensor is a passive RFID tag, comprising a chip and an antenna, and which can no longer be read when the value of at least one physical quantity exceeds a threshold value.

19. The device according to claim 18, characterized in that at least one said sensor is arranged in the container.

20. The device according to claim 18, characterized in that at least one said sensor is arranged in a housing provided in said container.

* * * * *